United States Patent [19]

Rencher et al.

[11] Patent Number: 5,451,409
[45] Date of Patent: Sep. 19, 1995

[54] SUSTAINED RELEASE MATRIX SYSTEM USING HYDROXYETHYL CELLULOSE AND HYDROXYPROPYL CELLULOSE POLYMER BLENDS

[76] Inventors: William F. Rencher, 9455 Misty Grove Cove, Cardova, Tenn. 38018; Suresh Babu, 6 Upper Field Rd., Morristown, N.J. 07960; Shankar Musunuri, 7565 Charmant Dr., #508, San Diego, Calif. 92122; Christopher H. Day, 237 Bridge St., Spring City, Pa. 19475; James Schwing, 304 Central Ave., Langhorne Manor, Pa. 19047

[21] Appl. No.: 156,223

[22] Filed: Nov. 22, 1993

[51] Int. Cl.⁶ .................................................. A61K 9/22
[52] U.S. Cl. ..................... 424/468; 424/469; 424/480; 424/484; 424/488; 424/494; 514/963; 514/964; 514/965
[58] Field of Search .............. 424/468, 469, 480, 484, 424/488, 494; 514/963, 964, 965

[56] References Cited

U.S. PATENT DOCUMENTS

| | | | |
|---|---|---|---|
| 4,226,848 | 10/1980 | Nagal et al. | 424/434 |
| 4,235,870 | 11/1980 | Leslie | 424/480 |
| 4,250,163 | 2/1981 | Nagal et al. | 424/434 |
| 4,260,596 | 4/1981 | Mackles | 426/548 |
| 4,284,957 | 8/1981 | Haque | 330/253 |
| 4,369,172 | 1/1983 | Schor et al. | |
| 4,427,681 | 1/1984 | Munshi | 424/468 |
| 4,449,983 | 5/1984 | Cortese et al. | 604/892 |
| 4,558,051 | 12/1985 | Sunshine et al. | 514/264 |
| 4,601,894 | 7/1986 | Hanna et al. | 514/781 |
| 4,610,870 | 9/1986 | Jain et al. | 424/480 |
| 4,657,757 | 4/1987 | Hanna et al. | 514/781 |
| 4,678,516 | 7/1987 | Alderman | 514/967 |
| 4,695,591 | 9/1987 | Hanna et al. | 514/781 |
| 4,704,285 | 11/1987 | Alderman | 424/468 |
| 4,777,050 | 10/1988 | Vadino | 424/468 |
| 4,789,549 | 12/1988 | Khan et al. | 424/468 |
| 4,927,639 | 5/1990 | Ghebre-Sellassie et al. | 424/468 |
| 5,002,774 | 3/1991 | Agrawala et al. | 424/468 |
| 5,085,865 | 2/1992 | Nayak | 424/480 |
| 5,284,662 | 2/1994 | Koparkar et al. | 424/473 |

FOREIGN PATENT DOCUMENTS

0111144  6/1984  European Pat. Off. .

OTHER PUBLICATIONS

D. A. Alderman, "A Review of Cellulose Ethers in Hydrophilic Matrices for Oral Controlled Release Dosage Forms", Int. J. Pharm., Tech & Prod. Fr. 5 (3) 1–9, 1984.

*Primary Examiner*—Ronald W. Griffin
*Attorney, Agent, or Firm*—Hal Brent Woodrow

[57] ABSTRACT

The present invention is directed to a novel sustained release matrix and oral dosage form comprising a homogeneous matrix formed from a wet granulation containing an effective amount of a medicament and a polymer blend of hydroxypropyl cellulose and hydroxyethyl cellulose. The present invention also discloses a novel process for making a sustained release oral dosage form comprising wet granulating a medicament with a polymer blend of hydroxypropyl cellulose and hydroxyethyl cellulose to form a homogeneous matrix, wherein the polymer blend is provided in an amount effective to control the release of said medicament, then forming the homogenous matrix into a solid oral dosage form.

21 Claims, No Drawings

SUSTAINED RELEASE MATRIX SYSTEM USING HYDROXYETHYL CELLULOSE AND HYDROXYPROPYL CELLULOSE POLYMER BLENDS

FIELD OF THE INVENTION

This invention relates to a matrix-like solid dosage form comprising one or more therapeutic agents, hydroxyethyl cellulose (HEC) and hydroxypropyl cellulose (HPC) and other tablet excipients (binders, diluents and coloring agents). More particularly, this invention relates to a polymer blend of HEC and HPC that will release a therapeutic agent or agents for a prolonged or sustained time.

BACKGROUND OF THE INVENTION

Sustained or extended release dosage forms which comprise a single active component are well known. A matrix tablet system incorporates active ingredients, lubricants, binders, fillers and other excipients, wherein the binders may be hydrophilic, hydrophobic or water insoluble polymers. See for example U.S. Pat. No. 4,389,393.

The mechanism by which sustained release dosage forms act to dispense the active ingredients over a period of time have been described at length in the literature. See for example Manford Robinson, Chapter 14, "Sustained Action Dosage Forms," The Theory and Practice of Industrial Pharmacy, 2nd, ed., ed. L. Lachman, H. Lieberman and J. Kanig (Philadelphia; Lea & Febiger, 1976).

Sustained release dosage forms which combine two or more actives are not common, because of the difficulties encountered in combining multiple actives, each with different chemical and physical characteristics, different release rates, different half-lives and different dosage sizes. However, three U.S. Patents do exist which are directed to the sustained release of two or more actives.

U.S. Pat. Nos. 4,601,894, 4,657,757 and 4,695,591 describe controlled-release dosage forms which incorporate acetaminophen, pseudoephedrine sulfate and dextrobrompheniramine maleate with a polymeric material. Both U.S. Pat. Nos. 4,601,489 and 4,687,757 describe a controlled release system which contains hydroxypropyl methyl cellulose (HPMC) and a second polymer selected from the group consisting of ethyl cellulose, methyl cellulose, sodium carboxymethyl cellulose or other cellulose ethers. U.S. Pat. No. 4,695,591 describes a one component controlled release system containing only HPMC U.S.P. 2910.

However, none of these patents recognize that a superior controlled release dosage form can be obtained by incorporating one or more pharmaceutical actives in a polymeric matrix of hydroxypropyl cellulose (HPC) and hydroxyethyl cellulose (HEC).

SUMMARY OF THE INVENTION

We have discovered a novel sustained release oral dosage form comprising a homogeneous matrix formed from a wet granulation containing an effective amount of a medicament and a polymer blend of hydroxypropyl cellulose and hydroxyethyl cellulose.

In another embodiment of the present invention, we have discovered a novel process for making a sustained release oral dosage form comprising wet granulating a medicament with a polymer blend of hydroxypropyl cellulose and hydroxyethyl cellulose, wherein the polymer blend is provided in an amount effective to control the release of said medicament to form a homogeneous matrix, then forming the homogenous matrix into a solid oral dosage form.

These and other objects and advantages of the invention will be apparent from the specification examples and claims hereinafter.

DETAILED DESCRIPTION OF THE INVENTION

The sustained or extended release dosage form which is the subject of this invention represents an advancement of the art since it combines two polymer ingredients, one or more drugs and other tablet excipients, in a single long acting tablet. While antihistamines and decongestants have been combined in sustained release tablets, and antihistamines, decongestants and analgesics have been combined in 2-layer tablets or have been separately microencapsulated and combined in continuous action capsules, the present invention relates to a surprisingly simple combination of one or more actives in a single homogenous matrix, from which matrix each active component is released at an appropriate rate to provide the desired activity over a period of 2 to 24, preferably 8 to 12 hours.

The components of the matrix are preferably chosen so that a dosage form of the present invention releases the actives over precise periods of time.

The compounds of the matrix are preferably chosen so that each active component is released from the matrix at its desired rate despite the differences in solubilities among the actives in gastric, intestinal or aqueous media, indicating that different mechanisms of drug release, i.e. diffusion through, and erosion of the hydrated layer, are occurring simultaneously. The differences in dosage size will not affect the appropriate release of each of the actives. That is, the actives may take up the majority of the total uncoated tablet weight and deliver the desired sustained release rates for the active. It has also been demonstrated that one or more actives with significantly different biological half-lives each demonstrates its own efficacious pharmacological profile when combined in a single sustained release dosage form.

One or more medicaments may be combined in a single dosage form, depending on the chemical compatibility of the combined active ingredients and the ability to obtain the desired release rate from the dosage form for each active ingredient. The determination of the effective amount of the medicament per dosage unit is easily determined by skilled clinicians.

Representative types of active medicaments include antacids, anti-inflammatory substances, (including but not limited to non-steroidal anti-inflammatory drugs, NSAIDs, vasodilators, coronary vasodilators, cerebral vasodilators, and peripheral vasodilators), anti-infectives, psychotropics, antimanics, stimulants, antihistamines, laxatives, decongestants, vitamins, gastrointestinal sedatives, antidiarrheal preparations, antianginal drugs, antiarrhythmics, antihypertensive drugs, vasoconstrictors and migraine treatments, anticoagulants and anti-thrombotic drugs, analgesics, anti-pyretics, hypnotics, sedatives, antiemetics, anti-nauseants, anticonvulsants, neuromuscular drugs, hyper- and hypoglycemic agents, thyroid and antithyroid preparations, diuretics, antispasmodics, uterine relaxants, mineral and nutritional additives, anti-obesity drugs, anabolic drugs, erythropoietic drugs, antiasthmatics, expectorants, cough suppressants, mucolytics, antiuricemic drugs, and other drugs or substances acting locally in the mouth, such as topical analgesics, local anesthetics, etc. Preferably the active medicament will be at least very slightly soluble in water and more preferably slightly soluble in water (as defined in *Remington's Pharmaceutical Sciences,* 18th edition, Chapter 16, page 208).

Examples of specific active medicaments include aluminum hydroxide, prednisolone, dexamethasone, aspirin, acetaminophen, ibuprofen, isosorbide dinitrate, nicotinic acid, tetracycline, ampicillin, dexbrompheniramine, chlorpheniramine, albuterol, pseudoephedrine, loratadine theophylline, ascorbic acid, tocopherol, pyridoxine, metoclopramide, magnesium hydroxide, verapamil, procainamide hydrochloride, propranolol, captopril, ergotamine, flurazepam, diazepam, lithium carbonate, insulin, furosemide, hydrochlorothiazide, guaiphenesin, dextromethorphan and benzocaine, although any active medicament which is physically and chemically compatible with the hydroxypropyl cellulose and hydroxyethyl cellulose polymer blend and other tablet ingredients and which demonstrates the desired controlled release characteristics may be used in the present invention.

Formulations containing NSAIDs (including for the purposes of this application acetaminophen) may also contain therapeutic amounts of other pharmaceutical actives conventionally employed with NSAID including but not limited to decongestants or bronchodilators (such as pseudoephedrine, phenylpropanolamine, phenylephrine and pharmaceutically acceptable salts thereof), antitussives (such as caraminophen, dextromethorphan and pharmaceutically acceptable salts thereof), antihistamines (such as chlorpheniramine, brompheniramine, dexchlorpheniramine, dexbrompheniramine, triprolidine, doxylamine, tripelennamine, cyproheptadine, pyrilamine, hydroxyzine, promethazine, azatadine and pharmaceutically acceptable salts thereof), non-sedating antihistamines (such as acrivastine, astemizole, cetirizine, ketotifen, loratidine, temelastine, terfenadine (including the metabolites disclosed in U.S. Pat. Nos. 4,254,129 and 4,285,957 hereby incorporated by reference and pharmaceutically acceptable salts thereof), muscle relaxants (such as glycerylmonether SMRS, methocarbamol, mephenesin, mephenesin carbamate, cyclobenzaprine, chlorzoxazone, mephenesin acid succinate, chlorphenesin carbamate, or pharmaceutically acceptable salts thereof) and suspected adjuvants (such as diphenhydramine, caffeine, xanthine derivatives (including those disclosed in U.S. Pat. No. 4,558,051, hereby incorporated by reference) and pharmaceutically acceptable salts thereof) and combinations of any of the aforesaid pharmaceutical. The aforesaid pharmaceutical may be combined with acetaminophen for the treatment of allergies, cough, colds, cold-like and/or flu symptoms in mammals including humans. However, these pharmaceutical maybe combined with acetaminophen as sleep aids (such as diphenhydramine), or for other known purposes.

The specific preferred combination of HPC and HEC of the invention with two or more actives provides a single sustained release medicament which provides the pharmacologic properties of each active. Thus, repeated administration of several single component dosage forms throughout the day may be avoided. Moreover, it is apparent that in addition to the well known pharmacological advantages of a controlled release formulation in general (e.g. more constant blood levels of the drugs), the dosage form of the present invention is easier and more economical to manufacture than microencapsulated or multi-layered dosage forms.

While a number of polymers might be used as a binder for the matrix, this invention particularly contemplates the use of combinations of hydroxypropyl cellulose (HPC) and hydroxyethyl cellulose (HEC). A single HPC ether may be used, or a mixture of HPC ethers of difference molecular weight and structure may be used. A single HEC ether may be used, or a mixture of HEC ethers of difference molecular weight and structure may be used. Suitable grades of HPC and HEC for pharmaceutical purposes are well known and full described in the pharmaceutical literature. Suitable commercially available brands of HPC include but are not limited Klucel TM hydroxypropyl cellulose (produced by Aqualon). Suitable commercially available brands of HEC include but are not limited to Natrosol TM hydroxyethyl cellulose (produced by Aqualon).

Generally the amount HPC and HEC and ratio of HPC to HEC used in a particular dosage formulation will vary based on the active medicament and the sustained release profile desired. However, the appropriate amount and ratios of HPC and HEC can readily be determined by systematically testing the dissolution profiles of the active medicament using accepted dissolution test such as those set forth in the *U.S. Pharmacopeia XXII* (hereby incorporated by reference).

As a general rule the weight range of HPC (or a mixture of HPC ethers) to HEC (or a mixture of HEC ethers) in a solid uncoated dosage form should be in the range of from about 10:90 to about 90:10 (wherein the total of HPC and HEC is 100 weight percent). A preferred combination of HEC and HPC for 8 hour sustained release contains from in the range of from 20 to 37.5 weight percent HEC and from in the range of from 80 to 62.5 weight percent HPC. A preferred combination of HEC and HPC for 12 hour SR tablets contains from in the range of from 62.4 to 37.6 weight percent HEC and from in the range of 62.4 to 37.6 weight percent HPC. A preferred combination of HEC and HPC for 24 hour SR tablets contains from in the range of from 62.5 to 75 weight percent HEC and from in the range of 37.5 to 25 weight percent HPC. With this dual system the total amount of HPC and HEC represents in the range of from about 5 to about 35 percent by weight of the total weight of an uncoated dosage form. A preferred range for the total amount of HPC and HEC present for the 8 hour sustained release (SR) tablet is 5 to 10 percent, for the 12 hour SR tablet 10 to 15 percent and for the 24 hour SR tablet is 12 to 18 percent by weight of the uncoated dosage form.

Additionally present with the HPC, HEC and active medicament may be one or more fillers or bulking agents such as dibasic calcium phosphate dihydrate, lactose or starch, with lactose being the preferred filler. The filler may be present in an amount in the range of from about 0 to about 94 percent of the total weight of the uncoated dosage from, with in the range of from about 1 to about 5 weight percent being preferred for very high dose actives and in the range of from about 80 to 85 weight percent with very low dose actives.

The uncoated dosage form may also contains one or more lubricating agents, e.g., stearic acid, colloidal silicon dioxide, magnesium stearate, calcium stearate, waxes, polyethylene glycol, or magnesium lauryl sulfate, present in an amount of in the range of from about 0.25 to about 3 weight percent of the total weight of the uncoated dosage form.

Other excipients, such as disintegrating agents, coloring agents and flavorings may be added at the discretion of those skilled in the art.

One example of a suitable 12 hour controlled release formulation for a cold or allergy tablet would contain:

TABLE 1

|  | RANGE | PREFERRED[1] RANGE |
|---|---|---|
| INGREDIENTS |  |  |
| HPC[2] | 5–12 | 3–8 |
| HEC[3] | 2–5 | — |
| Acetaminophen[4] | 20–89 | — |
| Pseudoephedrine Sulfate[4] | 3–15 | — |
| Chlorpheniramine Maleate[4] | 0.1–10 | — |
| EXCIPIENTS |  |  |
| Binder | 0.5–10 | — |
| Lubricant | 0.25–2.0 | — |
| Bulking Agent | 0–60 | — |

[1]Ranges are provided in percent by weight to the total weight of the uncoated caplet core or tablet.
[2]High or low viscosity HPC may be used for this formulation.
[3]It is preferred that high molecular weight HEC be used in this formulation.
[4]The dosage of active medicament may be adjusted to provide a larger or smaller therapeutical dose depending on the desired therapeutic effect and the intended recipient (adult or child).
[5]Suitable excipients are described in the Handbook of Pharmaceutical Excipients, Boylan, J.C. et al. Ed.; American Pharmaceutical Association; Washington, D.C., 1986 and Lieberman, H.A. et al. Pharmaceutical Dosage Forms:Tablets 2nd ed.; Marcel Dekker, New York, N.Y 1990 (both hereby incorporated by reference).

Another suitable 12 hour controlled release allergy formulation would contain:

TABLE 2

|  | Broad Range |
|---|---|
| Ingredients |  |
| HPC[2] | 3–8 |
| HEC[3] | 4–8 |
| Terfenadine[4] | 3–15 |
| Acetaminophen[4] | 20–88 |
| Excipients[5] |  |
| Binder | 0.5–10 |
| Disintegrants | 0.5–5 |
| Lubricant | 0.25–2.0 |
| Bulking Agent | 0–60 |

[1]Ranges are provided in percent by weight to the total weight of the uncoated caplet core or tablet.
[2]High or low viscosity HPC may be used for this formulation.
[3]It is preferred that high molecular weight HEC be used in this formulation.
[4]The dosage of active medicament may be adjusted to provide a larger or smaller therapeutical dose depending on the desired therapeutic effect and the intended recipient (adult or child).
[5]Suitable excipients are described in the Handbook of Pharmaceutical Excipients, Boylan, J.C. et al. Ed.; American Pharmaceutical Association; Washington, D.C., 1986 and Lieberman, H.A. et al. Pharmaceutical Dosage Forms:Tablets 2nd ed.; Marcel Dekker, New York, N.Y 1990 (both hereby incorporated by reference). Preferred binders include HPMC and PVP K-29/32.

One suitable 8 hour controlled release allergy formulation would contain:

TABLE 3

|  | Broad Range |
|---|---|
| Ingredients |  |
| HPC[2] | 5–10 |
| HEC[3] | 1–4 |
| Acetaminophen[4] | 20–90 |
| Pseudoephedrine Hydrochloride[4] | 3–15 |
| Excipients[5] |  |
| Binder | 0.5–10 |
| Disintegrants | 0.5–5 |

TABLE 3-continued

|  | Broad Range |
|---|---|
| Lubricant | 0.25–2.0 |
| Bulking Agent | 0–60 |

[1]Ranges are provided in percent by weight to the total weight of the uncoated caplet core or tablet.
[2]High or low viscosity HPC may be used for this formulation.
[3]It is preferred that high molecular weight HEC be used in this formulation.
[4]The dosage of active medicament may be adjusted to provide a larger or smaller therapeutical dose depending on the desired therapeutic effect and the intended recipient (adult or child).
[5]Suitable excipients are described in the Handbook of Pharmaceutical Excipients, Boylan, J.C. et al. Ed.; American Pharmaceutical Association; Washington, D.C., 1986 and Lieberman, H.A. et al. Pharmaceutical Dosage Forms:Tablets 2nd ed.; Marcel Dekker, New York, N.Y 1990 (both hereby incorporated by reference).

The above components are combined to form the matrix and formed into tablets by conventional means. The tablets may be used as is, but are preferably coated by techniques well known in the art. The sustained-release solid dosage form can be made by direct compression or through conventional wet granulation methods. Although differences in the dissolution profile may be observed by employing wet granulation rather than direct compression. Lower polymer concentrations may be used in the tablet when wet granulation processing. Because high-viscosity polymers are often preferred for sustained release, the normal wet granulation method of first dissolving the polymer may not be possible. However, if one of the two polymers is low viscosity, adding the lower viscosity polymer in solution is often advantageous for better tablet binding. Very acceptable granulations can be made in conventional equipment by dry-blending all the ingredients and adding water or organic solvents as the granulating fluid in conventional equipment. It has also been shown that fluid bed granulation will work. One of the polymers in solution or an additional polymeric binder solution may be necessary to make good, non-friable granules. These granulation processes can be successfully used to improve flow of the powders and increase tablet hardness.

The invention will now be described in greater detail by reference to the following non-limiting examples.

EXAMPLE I

This example describes nine different formulations of a solid oral dosage form containing several active medicaments and a variety of HPC, HEC and HPC/HEC polymer concentrations.

Nine formulations (A–I) containing pseudoephedrine sulfate, chlorpheniramine maleate, magnesium stearate and optionally acetaminophen and dicalcium phosphate were prepared. Various amount of HEC (Natrosol HH) and/or HPC (Klucel HF) were added to the formulations as described below in Tables 4 and 5.

TABLE 4

Natrosol 250HH and Klucel HF at various Polymer Concentrations Compressed with Other Excipients Provide 8-9 hours of Pseudoephedrine HCl Sustained Release

| Sample Formulation | A | B | C | D | E | F |
|---|---|---|---|---|---|---|
|  | Natrosol 250HH | | Klucel HF | | | Natrosol: Klucel Ratio |
| Weight Percent | 25 | 35 | 15 | 25 | 35 | 10:10 |
| Dry Granulation Formulation |  |  |  |  |  |  |
| Pseudoephedrine | 120 | 120 | 120 | 120 | 120 | 60 |
| Natrosol 250HH | 126 | 177 | — | — | — | 90 |

TABLE 4-continued

Natrosol 250HH and Klucel HF at various
Polymer Concentrations Compressed with
Other Excipients Provide 8-9 hours of
Pseudoephedrine HCl Sustained Release

| Sample Formulation | A | B | C | D | E | F |
|---|---|---|---|---|---|---|
| Klucel HF | — | — | 61 | 101 | 142 | 90 |
| Acetaminophen | — | — | — | — | — | 650 |
| Chlorpheniramine Maleate | — | — | 8 | 8 | 8 | 4 |
| Dicalcium Phosphate | 254 | 203 | 211 | 171 | 130 | — |
| Mag. Stearate | 5 | 5 | 5 | 5 | 5 | 5 |
| Total Tablet Weight (mg per tablet): | 505 | 505 | 405 | 405 | 405 | 899 |

TABLE 5

Natrosol 250HH and Klucel HF at various
Polymer Concentrations Wet Granulated
with Other Excipients Provide 8-9 hours
of Pseudoephedrine HCl Sustained Release

| Sample Formulation | G | H | I |
|---|---|---|---|
|  | Natrosol 250HH | Klucel HF | Natrosol: Klucel Ratio |
| Weight Percent Wet Granulation Formulation | 12% | 10% | 2.5:5% |
| Pseudoephedrine | 60 | 60 | 60 |
| Natrosol 250HH | 98 | — | 19 |
| Klucel HF | — | 80 | 39 |
| Acetaminophen | 650 | 650 | 650 |
| Chlorpheniramine Maleate | 4 | 4 | 4 |
| Mag. Stearate | 4 | 4 | 4 |
| Total Tablet Weight (mg per tablet): | 816 | 798 | 776 |

The formulations A–F in Table 4 were direct compression granulations. The formulations in Table 5 were wet granulated and oven dried (to approximately 1.25% L.O.D.). All the granulations were compressed into tablets with a main compression force of 4,000 pounds. The tablets were then tested to determine their dissolution profiles. The dissolution tests were conducted in distilled water at 37° C. with a 50 rpm stirring rate using USP Dissolution Method II with paddles.

Table 6 provides a comparison of the effects of the various combinations of HPC and HEC on the dissolution profiles of pseudoephedrine sulfate.

TABLE 6

RELEASE PROFILE FOR PSEUDOEPHEDRINE

| | G | A | B | H | C | D | E | I | F |
|---|---|---|---|---|---|---|---|---|---|
| | Natrosol HEC only | | | Klucel HPC Only | | | | Natrosol and Klucel | |
| Weight Percentage | | | | | | | | | |
| | 12% | 25% | 35% | 10% | 15% | 25% | 35% | 2.5:5% | 10:10% |
| Time Hours | | | | | | | | | |
| 0.5 | 26 | 22 | 29 | — | 25 | 20 | 15 | — | — |
| 1.0 | 40 | 39 | 38 | 100 | 45 | 38 | 30 | 46 | 100 |
| 2.0 | — | 65 | 59 | | 65 | 55 | 42 | — | |
| 3.0 | 70 | 75 | 65 | | 85 | 75 | 55 | 76 | |
| 5.0 | — | 77 | 82 | | 100 | 95 | 75 | — | |
| 6.0 | 87 | 78 | 85 | | | 100 | 88 | 97 | |
| 8.0 | 93 | 88 | 95 | | | | 95 | 100 | |

As can be seen from Table 6 the wet granulation of 2.5 weight percent HEC and 5 weight percent HPC provided a significantly prolonged release profile for pseudoephedrine as compared to tablets containing HPC only at 10%, 15% and 25%. Approximately five times the amount of HEC (Natrosol 250 HH) was necessary to provide the same release profile as the combination of 2.5 weight percent HEC and 5 weight percent HPC. It appears from the data that wet granulations of HPC and HEC at 2.5 to 5.0 weight percent provide prolonged sustained release profile for pharmaceutical actives which was not previously recognized in the art.

EXAMPLE 2

This example describes three different formulations of a solid oral dosage form containing three active medicaments and a variety of HPC, HEC and HPC/HEC polymer concentrations.

Three formulations (J, K and L) containing 650 mg acetaminophen, 4 mg chlorpheniramine maleate and 60 mg pseudoephedrine sulfate and were lubricated with 0.5% stearic acid and 0.25% Cab-o-sil were prepared. Various amount of HEC (Natrosol HH) and/or HPC (Klucel HF) were added to the formulations as described below in Table 7.

TABLE 7

HPC (Klucel HF) and HEC (Natrosol 250 HH) Combination or Alone, in Tablets containing Acetaminophen, Chlorpheniramine Maleate and Pseudoephedrine Sulfate.

| Polymers | Formula: | J | K | L |
|---|---|---|---|---|
| Natrosol HH HEC (wt. %) | | 0 | 5 | 5 |
| Klucel HF HPC (wt. %) | | 5 | 0 | 5 |

The formulations were wet granulated (with water) using high shear equipment and oven dried (to approximately 1.25% L.O.D.). The dried granulations were milled and lubricated. The granulations were then compressed into equal strength tablets. Formulas J and L granulations were compressed with a main compression force of 20 kN into tablets. Formula K required precompression (2.5 kN) and main compression (28 kN) for adequate tablet hardness. The tablets were then tested to determine their dissolution profiles. The dissolution tests were conducted in distilled water at 37° C. with a 50 rpm stirring rate using USP Dissolution Apparatus 2 or Hanson Dissolution Apparatus with paddles.

Table 8 provides a comparison of the dissolution profiles of acetaminophen, pseudoephedrine sulfate and chlorpheniramine maleate.

TABLE 8

| Drug | Time (Hrs.) | Percent Drug Release | | |
|---|---|---|---|---|
| | | J | K | L |
| APAP[1] | 1 | 90 | 50 | 14 |
| | 3 | 100 | 66 | 26 |
| | 6 | | 82 | 43 |
| | 8 | | 90 | 50 |
| | 12 | | 100 | 65 |
| PE[2] | 1 | 90 | ND | 23 |
| | 3 | 100 | >90 | 45 |
| | 6 | | 100 | 65 |
| | 8 | | | 78 |
| | 12 | | | 93 |
| CPM[3] | 1 | 90 | ND | 38 |
| | 3 | 100 | 100 | 63 |
| | 6 | | | 82 |
| | 8 | | | 93 |

TABLE 8-continued

| | | Percent Drug Release | | |
|---|---|---|---|---|
| Drug | Time (Hrs.) | J | K | L |
| | 12 | | | 100 |

[1]Acetaminophen
[2]Pseudoephedrine sulfate
[3]Chlorpheniramine maleate

The data presented in Table 8 demonstrates that the combination of HPC and HEC provide a sustain release profile to various active medicaments.

EXAMPLE 3

This example demonstrates the effect of using high and low viscosity HEC in controlled release formulation which contain HPC and a therapeutic medicament
Two formulation (M and N) were prepared containing the ingredients listed in Table 9.

TABLE 9

| Low Viscosity HEC M | Wt.% | High Viscosity HEC N | Wt. % |
|---|---|---|---|
| Klucel HF | 6 | Klucel HF | 5 |
| Natrosol 250L | 2 | Natrosol 250HH | 2.5 |
| APAP | 84 | APAP | 84 |
| Pseudoephedrine | 7.5 | Pseudoephedrine | 8 |
| Lubricants | 0.5 | Lubricants | 0.5 |

The ingredients were wet granulated and compressed with a main compression force of 20 kN into tablets which would deliver 650 mg of APAP and 60 mg of PE. The dissolution of the tablets were then tested using USP Dissolution Apparatus 2 with paddles containing distilled water maintained at 37° C. with a 50 rpm stirring rate. The results of these tests are reported in Table 10.

TABLE 10

| TIME (Hours) | FORMULA M | FORMULA N |
|---|---|---|
| PERCENT ACETAMINOPHEN RELEASE | | |
| 1 | 47 | 21 |
| 3 | 79 | 41 |
| 6 | 100 | 68 |
| 8 | | 82 |
| 12 | | 95 |
| PERCENT PSEUDOEPHEDRINE RELEASE | | |
| 1 | 61 | 47 |
| 3 | 93 | 75 |
| 6 | 100 | 95 |
| 8 | | 100 |

The results reported in Table 10 demonstrate that both high and low viscosity HEC maybe used in the practice of the present invention. It is apparent from the data, however, that the high viscosity HEC has a greater sustained release affect as compared to low viscosity HEC. Those skilled in the art will readily appreciate that the HEC viscosity can be varied for particular medicaments to provide the desired release profile.

EXAMPLE 4

This example demonstrates the effect of increasing the polymers content of HEC/HPC on the dissolution profile of acetaminophen.
Three formulations (O, P and Q) containing 650 mg acetaminophen, 4 mg chlorpheniramine maleate and 60 mg pseudoephedrine sulfate, 0.5% stearic acid, 0.25% Cab-o-sil and varying amounts of HPC (Klucel) and HEC (Natrosol HH) were prepared. The amount of HEC (Natrosol HH) and/or HPC (Klucel HF) added to the formulations is described below in Table 11.

TABLE 11

| | WEIGHT OF INGREDIENTS (mg) | | |
|---|---|---|---|
| FORMULA | O | P | Q |
| Natrosol 250HH (HEC) | 5 | 10 | 15 |
| Klucel HF (HPC) | 5 | 10 | 15 |
| Acetaminophen | 650 | 650 | 650 |
| Pseudoephedrine Sulfate | 60 | 60 | 60 |
| Chlorpheniramine Maleate | 4 | 4 | 4 |

The ingredients were wet granulated and compressed with a main compression force of 20 kN into tablets. The dissolution of the tablets were then tested using a USP Dissolution Apparatus 2 containing simulated intestinal fluid without pancreatic enzymes maintained at 37° C. The dissolution test was conducted with a stirring rate of 50 rpm. The results of these tests are reported in Table 12.

TABLE 12

| | PERCENT ACETAMINOPHEN RELEASE | | |
|---|---|---|---|
| TIME(Hours) | O | P | Q |
| 1 | 20 | 20 | 20 |
| 3 | 45 | 43 | 32 |
| 6 | 73 | 57 | 46 |
| 8 | 85 | 66 | 57 |
| 12 | 100 | 80 | 75 |

The data in Table 12 demonstrates that by increasing the amount of HEC and HPC used in the tablet formulations, the duration of the sustained release effect may be lengthened.

EXAMPLE 5

This example provides a preferred formulation for a 12 hour cold/allergy caplet. This caplet is preferably made using a high shear granulation process.

TABLE 13

| TABLET CORE FORMULA: | | |
|---|---|---|
| | | PERCENTAGE |
| POLYMER | VISCOSITY | |
| HPC | High (or Lower) | 5 |
| HEC | Very High | 2.5 |
| PVP | K-29/32 | 1 |
| ACTIVES | | |
| Acetaminophen USP Powder | | 82.1 |
| Pseudoephedrine Sulfate | | 7.6 |
| Chlorpheniramine Maleate | | 0.5 |
| EXCIPIENTS | | |
| Stearic Acid | | 1.0 |
| Colloidal Silicon Dioxide | | 0.5 |
| Water* | | — |

*Water was used in making the granulation solutions containing the polymer(s).

EXAMPLE 6

This example provides a preferred formulation for a 8 hour sinus caplet containing acetaminophen and pseudoephedrine. This caplet is preferably made using a high shear granulation process.

TABLE 14

| TABLET CORE FORMULA: | |
|---|---|
| | PERCENTAGE |
| POLYMER | VISCOSITY |

TABLE 14-continued

TABLET CORE FORMULA:

| | | PERCENTAGE |
|---|---|---|
| HPC | High (or Lower) | 6 |
| HEC | Very High | 2 |
| PVP | K-29/32 | 1 |
| ACTIVES | | |
| Acetaminophen USP Powder | | 82.4 |
| Pseudoephedrine Sulfate | | 5.1 |
| EXCIPIENTS | | |
| Sodium Starch Glycolate | | 2 |
| Stearic Acid | | 1 |
| Colloidal Silicon Dioxide | | 0.5 |
| Water* | | — |

*Water was used in making the granulation solutions containing the polymer(s).

EXAMPLE 7

This example provides a preferred formulation for a 12 hour sinus caplet containing terfenadine and acetaminophen. This caplet is preferably made using a high shear granulation process.

TABLE 15

| INGREDIENTS | | PERCENTAGE |
|---|---|---|
| IMMEDIATE RELEASE LAYER | | |
| Terfenadine | | 8.2 |
| Acetaminophen | | 82.3 |
| HPMC Low Viscosity | | 3 |
| Microcrystalline Cellulose (Avicel PH 101) | | 3 |
| Sodium Starch Glycolate | | 3 |
| Magnesium Stearate | | 0.5 |
| Water* | | — |
| SUSTAINED RELEASE LAYER | | |
| POLYMER | VISCOSITY | |
| HPC | Low or High* | 5 |
| HEC | High | 7.5 |
| PVP | K-29/32 | 1 |
| ACTIVE | | |
| Acetaminophen USP Powder | | 86 |
| EXCIPIENTS | | |
| Magnesium Stearate | | 0.5 |
| Water* | | — |

*Water was used in making the granulation solutions containing the polymer(s).

We claim:

1. A sustained release pharmaceutical matrix comprising a homogeneous matrix containing a therapeutically effective amount of a medicament and a polymer blend of hdyroxypropyl cellulose (HPC) and hydroxyethyl cellulose (HEC) provided in an amount of about 18 weight percent or less to provide a sustained release of said medicament, wherein the ratio of HPC to HEC is in the range from about 10:90 to about 90:10.

2. The matrix of claim 2 wherein the polymer blend contains in the range of from 80 to 62.5 weight percent HPC and in the range of from 20 to 37.5 weight percent HEC.

3. The matrix of claim 2 wherein the polymer blend contains in the range of from 62.4 to 37.6 weight percent HPC and in the range of from 37.6 to 62.4 weight percent HEC.

4. The matrix of claim 2 wherein the polymer blend contains the range of from 62.5 to 75 weight percent HEC and in the range of from 37.5 to 25 weight percent HPC.

5. The matrix of claim 1 wherein the medicament is selected from the group consisting of antacids, anti-inflammatory drugs, vasodilators, anti-infectives, psychotropics, antimanics, stimulants, antihistamines, laxatives, decongestants, vitamins, gastrointestinal sedatives, antidiarrheal preparations, antianginal drugs, antiarrhythmics, antihypertensive drugs, vasoconstrictor drugs, analgesics, anti-pyretics, hypnotics, sedatives, antiemetics, anti-nauseants, anticonvulsants, neuromuscular drugs, hyperglycemic agents, hypoglycemic agents, thyroid preparations, antithyroid preparations, diuretics, antispasmodics, uterine relaxants, mineral additives, anti-obesity drugs, anabolic drugs, erythropoietic drugs, antiasthmatics, expectorants, cough suppressants, mucolytics, antiuricemic drugs, and combinations of two or more thereof.

6. The matrix of claim 1 wherein the medicament is an NSAID and one or more medicaments selected from the group consisting of decongestants, bronchodilators, antitussives, non-sedating antihistamines, muscle relaxants, adjuvants and combinations of any of the aforesaid medicaments.

7. The matrix of claim 2 wherein the matrix comprises in the range of from about 5 to about 12 weight percent HPC; in the range of from about 2 to about 5 weight percent HEC; in the range of from about 20 to about 89 weight percent acetaminophen; in the range of from about 3 to about 15 weight percent pseudoephedrine sulfate; in the range of from about 0.1 to about 10 weight percent chlorpheniramine maleate; in the range of from about 0.5 to about 10 weight percent of a binder; in the range of from about 0.25 to about 2.0 weight percent of a lubricant; and in the range of from about 0 to about 60 weight percent of a bulking agent.

8. The matrix of claim 1 wherein the matrix comprises in the range of from about 3 to about 8 weight percent HPC; in the range of from about 4 to about 8 weight percent HEC; in the range of from about 20 to about 88 weight percent acetaminophen; in the range of from about 3 to about 15 weight percent terfenadine; in the range of from about 0.5 to about 5 weight percent of a disintegrant; in the range of from about 0.5 to about 10 weight percent of a binder; in the range of from about 0.25 to about 2 weight percent of a lubricant; and in the range of from about 0 to about 60 weight percent of a bulking agent.

9. The matrix of claim 1 wherein the matrix comprises in the range of from about 5 to about 10 weight percent HPC; in the range of from about 1 to about 4 weight percent HEC; in the range of from about 20 to about 90 weight percent acetaminophen; in the range of from about 3 to about 15 weight percent pseudoephedrine hydrochloride; in the range of from about 0.5 to about 5 weight percent of a disintegrant; in the range of from about 0.5 to about 10 weight percent of a binder; in the range of from about 0.25 to about 2 weight percent of a lubricant; and in the range of from about 0 to about 60 weight percent of a bulking agent.

10. A process for making a sustained release oral dosage form comprising wet granulating a medicament with a polymer blend of hydroxypropyl cellulose (HPC) and hydroxyethyl cellulose (HEC), wherein the polymer blend is provided in an amount of about 18 weight percent or less and the ratio of HPC to HEC is in the range of from about 10:90 to about 90:10, wherein the polymer blend is provided to control the release of said medicament, to form a homogeneous matrix, then forming the homogenous matrix into a solid oral dosage form.

11. The process of claim 10 wherein the polymer blend contains in the range of from 80 to 62.5 weight percent HPC and in the range of from 20 to 37.5 weight percent HEC.

12. The process of claim 10 wherein the polymer blend contains in the range of from 62.4 to 37.6 weight percent HPC and in the range of from 37.6 to 62.4 weight percent HEC.

13. The process of claim 10 wherein the polymer blend contains the range of from 62.5 to 75 weight percent HEC and in the range of from 37.5 to 25 weight percent HPC.

14. The process of claim 10 wherein the homogeneous matrix comprises in the range of from about 5 to about 12 weight percent HPC; in the range of from about 2 to about 5 weight percent HEC; in the range of from about 20 to about 89 weight percent acetaminophen; in the range of from about 3 to about 15 weight percent pseudoephedrine sulfate; in the range of from about 0.1 to about 10 weight percent chlorpheniramine maleate; in the range of from about 0.5 to about 10 weight percent of a binder; in the range of from about 0.25 to about 2 weight percent of a lubricant; and in the range of from about 0 to about 60 weight percent of a bulking agent.

15. The process of claim 10 wherein the homogeneous matrix comprises in the range of from about 3 to about 8 weight percent HPC; in the range of from about 4 to about 8 weight percent HEC; in the range of from about 20 to about 88 weight percent acetaminophen; in the range of from about 3 to about 15 weight percent terfenadine; in the range of from about 0.5 to about 5 weight percent of a disintegrant; in the range of from about 0.5 to about 10 weight percent of a binder; in the range of from about 0.25 to about 2 weight percent of a lubricant; and in the range of from about 0 to about 60 weight percent of a bulking agent.

16. The process of claim 10 wherein the homogeneous matrix comprises in the range of from about 5 to about 10 weight percent HPC; in the range of from about 1 to about 4 weight percent HEC; in the range of from about 20 to about 90 weight percent acetaminophen; in the range of from about 3 to about 15 weight percent pseudoephedrine hydrochloride; in the range of from about 0.5 to about 5 weight percent of a disintegrant; in the range of from about 0.5 to about 10 weight percent of a binder; in the range of from about 0.25 to about 2 weight percent of a lubricant; and in the range of from about 0 to about 60 weight percent of a bulking agent.

17. A sustained release oral dosage form comprising a homogeneous matrix containing a therapeutically effective amount of a medicament and a polymer blend of hydroxpropyl cellulose (HPC) and hydroxethyl cellulose (HEC) provided in an amount of not more than about 18 weight percent wherein the ratio of HPC to HEC is in the range of from about 10:90 to about 90:10, effective to provide a sustained release of said medicament in a solid oral dosage form.

18. The solid dosage form of claim 17 wherein the medicament is an NSAID and one or more medicaments selected from the group consisting of decongestants, bronchodilators, antitussives, antihistamines, non-sedating antihistamines, muscle relaxants, adjuvants and combinations of any of the aforesaid medicaments.

19. The oral dosage form of claim 17 wherein the dosage form comprises in the range of from about 5 to about 12 weight percent HPC; in the range of from about 2 to about 5 weight percent HEC; in the range of from about 20 to about 89 weight percent acetaminophen; in the range of from about 3 to about 15 weight percent pseudoephedrine sulfate; in the range of from about 0.1 to about 10 weight percent chlorpheniramine maleate; in the range of from about 0.5 to about 10 weight percent of a binder; in the range of from about 0.25 to about 2 weight percent of a lubricant; and in the range of from about 0 to about 60 weight percent of a bulking agent.

20. The oral dosage form of claim 17 wherein the dosage form comprises in the range of from about 3 to about 8 weight percent HPC; in the range of from about 4 to about 8 weight percent HEC; in the range of from about 20 to about 88 weight percent acetaminophen; in the range of from about 3 to about 15 weight percent terfenadine; in the range of from about 0.5 to about 5 weight percent of a disintegrant; in the range of from about 0.5 to about 10 weight percent of a binder; in the range of from about 0.25 to about 2 weight percent of a lubricant; and in the range of from about 0 to about 60 weight percent of a bulking agent.

21. The oral dosage form of claim 17 wherein the dosage form comprises in the range of from about 5 to about 10 weight percent HPC; in the range of from about 1 to about 4 weight percent HEC; in the range of from about 20 to about 90 weight percent acetaminophen; in the range of from about 3 to about 15 weight percent pseudoephedrine hydrochloride; in the range of from about 0.5 to about 5 weight percent of a disintegrant; in the range of from about 0.5 to about 10 weight percent of a binder; in the range of from about 0.25 to about 2 weight percent of a lubricant; and in the range of from about 0 to about 60 weight percent of a bulking agent.

* * * * *

UNITED STATES PATENT AND TRADEMARK OFFICE
CERTIFICATE OF CORRECTION

PATENT NO. : 5,451,409
DATED : September 19, 1995
INVENTOR(S) : William F. Rencher et al.

It is certified that error appears in the above-indentified patent and that said Letters Patent is hereby corrected as shown below:

Column 11, line 51, "of claim 2" should read -- of claim 1 --

Column 11, line 55, "of claim 2" should read -- of claim 1 --

Column 11, line 59, "of claim 2" should read -- of claim 1 --

Column 12, line 17, "of claim 2" should read -- of claim 1 --

Signed and Sealed this

Thirteenth Day of August, 1996

Attest:

BRUCE LEHMAN

*Attesting Officer*  *Commissioner of Patents and Trademarks*